United States Patent [19]

Cowan et al.

[11] 4,059,992
[45] Nov. 29, 1977

[54] APPARATUS FOR TESTING THE TENSILE STRENGTH OF SHEET MATERIAL

[75] Inventors: Wavell Frederick Cowan, Montreal West; Bote Bruinsma, Hudson, both of Canada

[73] Assignee: Pulmac Instruments Ltd., Montreal, Canada

[21] Appl. No.: 716,097

[22] Filed: Aug. 20, 1976

[30] Foreign Application Priority Data
May 31, 1976  Canada ............................... 253719

[51] Int. Cl.² .......................................... G01N 3/10
[52] U.S. Cl. .................................................. 73/95
[58] Field of Search ............... 73/95, 95.5, 103, 159

[56] References Cited

U.S. PATENT DOCUMENTS

| | | | |
|---|---|---|---|
| 3,318,142 | 5/1967 | Shoemaker | 73/95 |
| 3,707,119 | 12/1972 | Cowan | 73/95 |

Primary Examiner—Jerry W. Myracle
Attorney, Agent, or Firm—Alan Swabey & Co.

[57] ABSTRACT

An improved testing device for testing the tensile strength of sheet material, such as paper, including a first pair of vertically moving jaws mounted on a support and a second pair of vertically moving jaws hanging from the first support in a pendulum manner and adapted to be at a dead-center position with the second pair of jaws juxtaposed to the first pair of jaws and in contact therewith for gripping a sheet of material to be tested therebetween. Low pressure, large diameter, pneumatic cylinders are provided for moving the lower jaws of each pair upwardly towards the fixed jaws against a self-aligning cylindrical spring.

9 Claims, 5 Drawing Figures

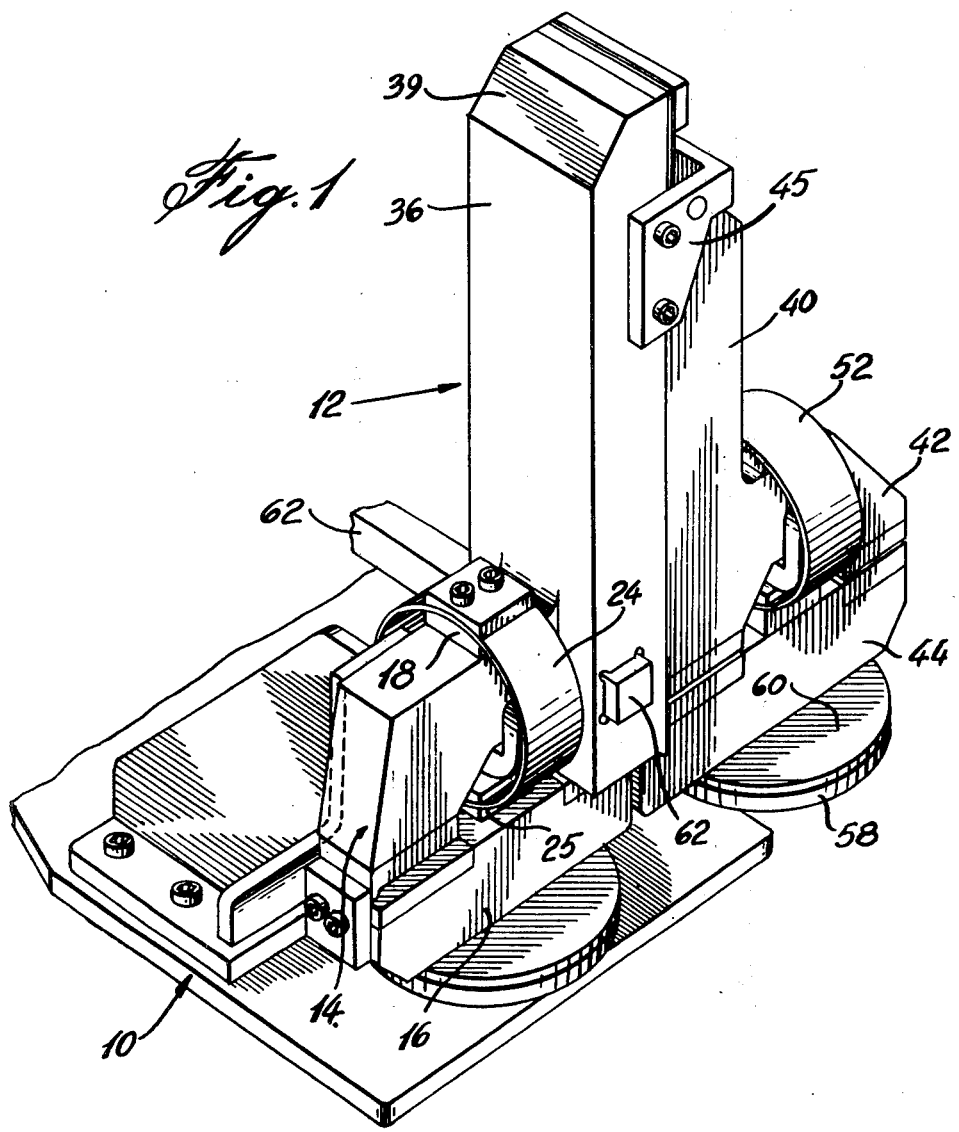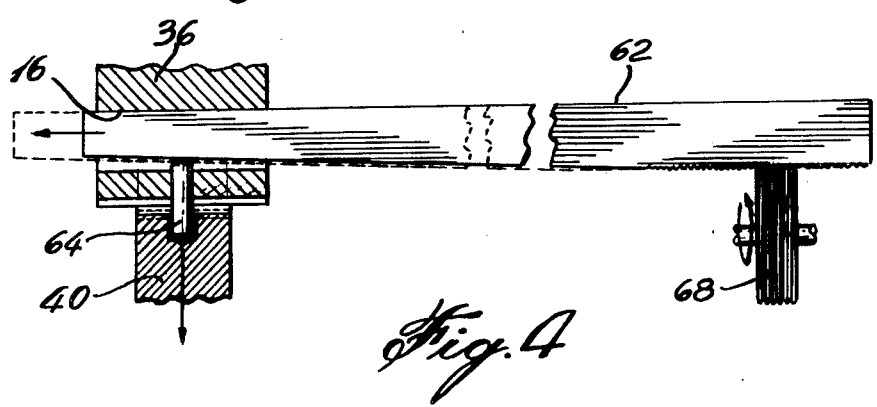

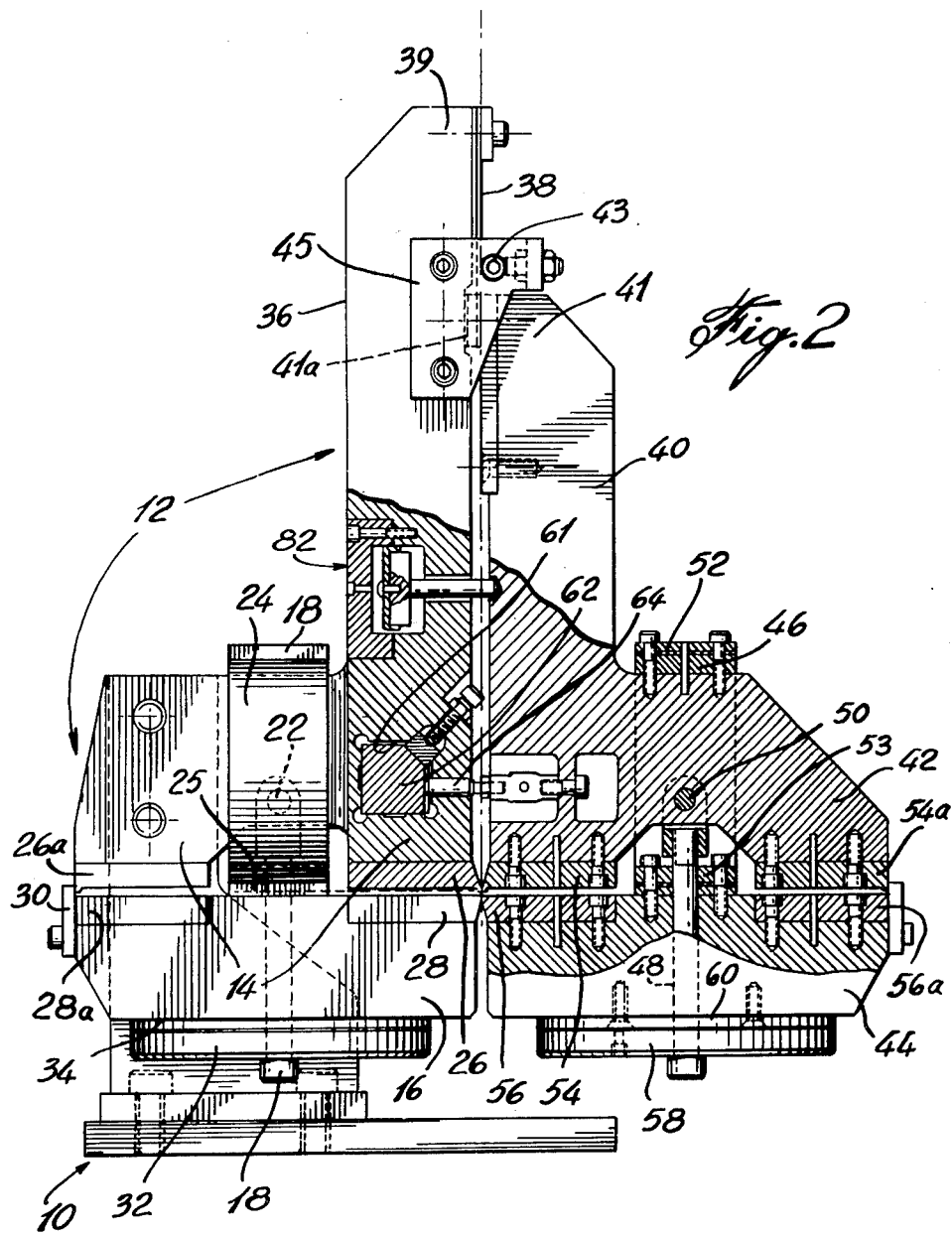

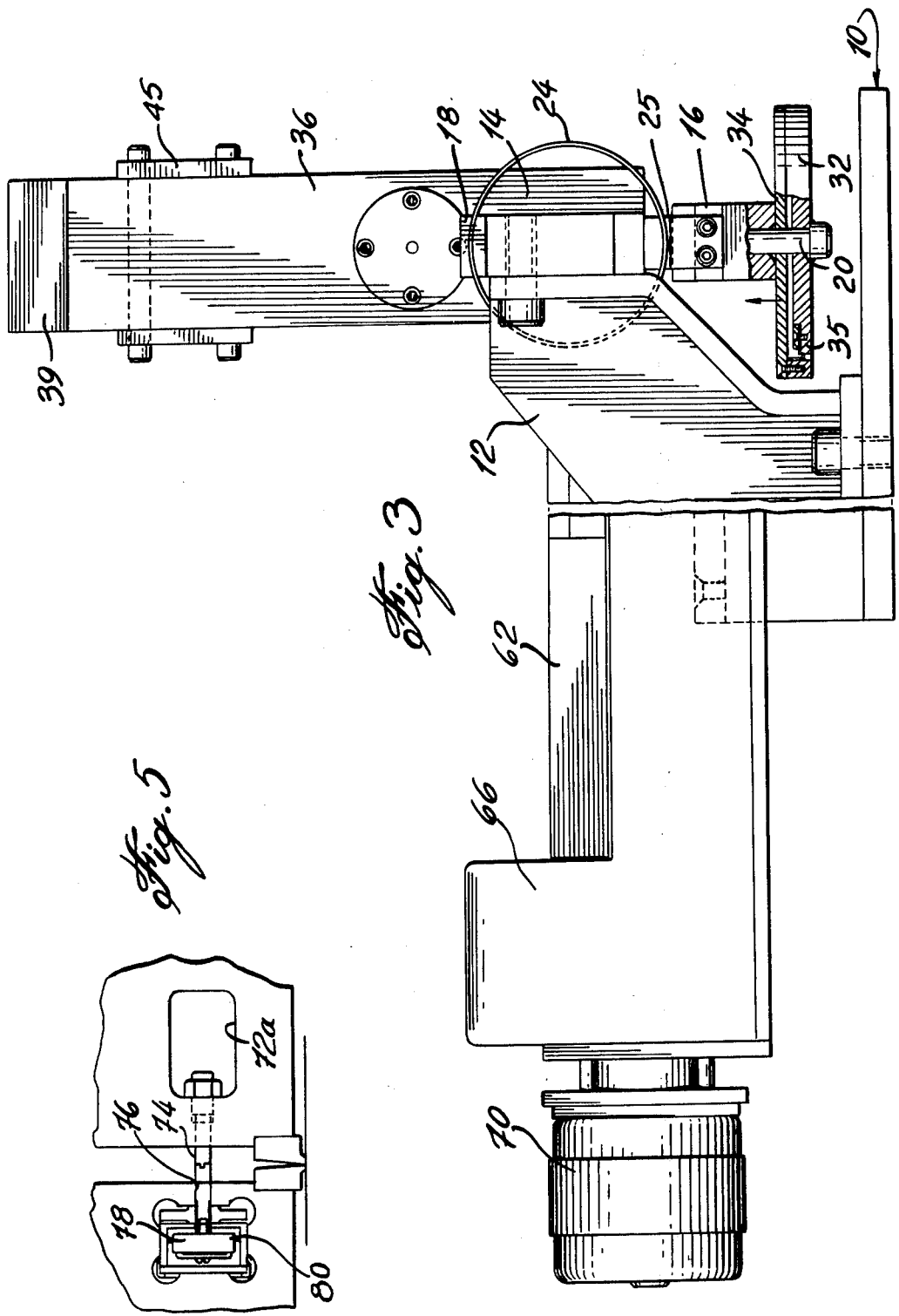

APPARATUS FOR TESTING THE TENSILE STRENGTH OF SHEET MATERIAL

BACKGROUND OF THE INVENTION

1. Field of the Invention

The present invention relates to an improved apparatus for testing the tensile strength of sheet material and in particular fibrous sheet material, such as paper.

2. Description of the Prior Art

Reference is made to U.S. Pat. No. 3,707,119, issued Dec. 26, 1972, by Wavell F. Cowan. In that patent an apparatus is described which comprises pairs of opposed clamping jaws wherein each pair of jaws is adapted to engage between them a portion of the sheet material adjacent that portion gripped by the opposed pair of jaws. Means are provided for controlling the pressure of each pair of clamping jaws on the sheet material. A support member is also provided for pivotally mounting one of the opposed pairs of clamping jaws relative to the other for pivotal movement between a first position whereby the opposed pairs of clamping jaws are juxtaposed in contact with each other and a position spaced apart from each other with the clamping jaws still gripping portions of the sheet. Motive means are provided for causing the pivotal movement of one pair of jaws relative to the other, said means including a fluid-operated piston and cylinder arrangement connected between the opposed pairs of jaws whereby a fluid load in the cylinder causes the opposed pairs of jaws to move away from said first position when the fluid load has overcome the tensile strength of the sheet gripped by the opposed pairs of jaws. Means are also provided for recording the fluid load required to overcome the tensile strength of the sheet material whereby the tensile strength of the sheet material can be conventionally measured.

It has been found that although the apparatus described in the above-mentioned patent performs with excellent results, it has been found, for one thing, that it cannot be used in situations of automatic continuous feeding since there is no clear through path through the jaws.

SUMMARY OF THE INVENTION

It is an aim of the present invention to provide an improved apparatus of the type described in U.S. Pat. No. 3,707,119 and which has increased versatility and improved performance capabilities.

A construction in accordance with the present invention for testing the tensile strength of fibers in a flat sheet comprises a base, a first support member on said base, a first pair of clamping jaws mounted to said first support member adapted to receive and clamp a sheet material to be tested, said first support member extending above said first pair of jaws, a second support member pivoted to said first support member in pendulum manner, a second pair of clamping jaws mounted on said second support member opposite to said first pair of jaws and adapted to clamp said sheet material adjacent said first pair of jaws, said second support member pivoting in a pendulum manner and being at dead center with said second pair of clamping jaws being juxtaposed with and in contact with the first jaws, means for pivotally causing the movement of the second support member away from dead center such that the pairs of jaws, while still clamping said sheet, move apart under pressure.

In another embodiment of the present invention, there is provided a means for pivotally causing the movement of the second support member away from the first member, including a through opening in said first member, an elongated wedge member of constantly increasing width adapted to move through said through opening, a push member fixed to said second member and adapted to abut against said wedge member such that, as the wedge passes through the through opening in ever increasing width, it moves said push member, thereby moving said second support member.

In a still further embodiment of the present invention, the pair of clamping jaws each include a cylindrical spring member maintaining the jaws in each pair apart.

BRIEF DESCRIPTION OF THE DRAWINGS

Having thus generally described the nature of the invention, reference will now be made to the accompanying drawings, showing by way of illustration, a preferred embodiment thereof, and in which:

FIG. 1 is a perspective view of the apparatus in accordance with the present invention;

FIG. 2 is a side elevation, partly in cross-section, of the apparatus shown in FIG. 1;

FIG. 3 is an end elevation thereof;

FIG. 4 is a schematic top plan view of a detail of the apparatus; and

FIG. 5 is a fragmentary detailed view of another embodiment of a feature of the present invention.

DESCRIPTION OF THE PREFERRED EMBODIMENTS

Referring now to the drawings, particularly FIGS. 1 to 4, there is shown a base 10 on which is mounted a support member 12. A top clamp jaw 14 is affixed directly to the support member 12 and a lower jaw member 16 is located underneath the top jaw member 14 and adapted for vertical movement to and from the top jaw 14 as will be described later.

A horizontal top bracket 18 is fixed to the top jaw member 14. A flexible cylindrical spring 24 made out of spring steel is fixed between the bracket 18 on the top jaw 14 and is in turn fixed to the lower jaw portion 16 by means of a bracket 25. The cylindrical spring 24 allows the lower jaw member 16 to move vertically in the same plane as the upper jaw 14 but prevents the jaw 16 from moving outward of the plane. The spring 24 will hold the lower jaw 16 in a position away from the upper jaw 14 such that when it is moved against the upper jaw 14, the spring 24 is under compression.

A suspension rod 20 is suspended from within jaw 14 by means of stub shaft 22. Mounted on the rod 20 is a large diamter pneumatic cylinder 32 with a similar large diameter telescoping cylinder 34. A diaphragm 35 (FIG. 3) is provided within the cylinder. The drum cylinder 34 is connected to the lower jaw 16, and when activated pneumatically, the drum cylinder 34 will extend away from the drum cylinder 32, moving the jaw 16 towards the jaw 14 against the spring 24. The top jaw member 14 mounts hardened jaw bits 26 and 26a, while the lower jaw 16 mounts hardened jaw bit insert 28, and at the other end there is an abutment 30 provided to allow the insert bit 26a to be guided thereagainst. The movement of the jaw 16 relative to the jaw 14 is parallel. However, the length of the jaws 14 and 16 is such that when a piece of sheet material such as paper is held between the jaw bits 26 and 28, the slight angular deviation from the parallel will not seriously deter from the clamping action. In the apparatus according to U.S. Pat. No. 3,707,119, it was found necessary, in view of the short length of the jaw members, to provide a blank member such as a sheet of the same thickness as the paper to be tested between the other ends of the jaws to allow parallel clamping of the jaws.

An upward extension of the upper jaw 14 provides a support 36 on which is mounted a spring bracket head 39 and clamping bracket 39a holding a steel spring member 38. Hanging from the steel spring plate 38 is the support member 40 which in turn is clamped to the spring plate 38 by means of a spring bracket head 41 and bracket clamp 41a. The construction of the jaw members mounted to support member 40 is similar to those just described. It is noted that the whole jaw assembly is suspended from the spring plate 38, and thus the support member 40 hangs in a pendulum manner. An adjustable fulcrum 43 is provided on a bracket 45 fixed to support 36.

Support member 40 is integral with the top jaw portion 42 onto which a top bracket 46 is fixed. The lower jaw member 44 moves in parallel motion in a vertical plane towards and away from the top jaw member 42. The top jaw member mounts clamping jaw bits 54 and 54a, while the lower jaw member 44 mounts jaw bits 56 and 56a.

A lower suspension rod 48 is suspended from the jaw member 42 by stub shaft 50. Pneumatic cylinders 58 and 60, with the cylinder 60 being fixed to the lower jaw member 44 and the cylinder 58 being mounted to the suspension rod 48, are provided in order to move the lower jaw member 44. The lower jaw member 44 is connected to a cylindrical spring member 52 by means of the bracket 53, while the portion of the spring member 52 diametrically opposed to the spring bracket 53 is fixed between the jaw member 42 and the top bracket 52.

The operation of the jaws 42 and 44 is similar to that of the jaws 14 and 16. The support member 40, including the jaw bits 54 and 56, hang at their dead center in the pendulum fashion when they are juxtaposed against the jaw bit members 26 and 28. In order to move the jaw bits 54 and 56 away from the jaw bits 26 and 28, it is necessary to oercome the weight of the jaw assembly hanging from the support member 40.

If it is necessary to maintain a constant rate of elongation, the following apparatus can be used. Elongated wedge member 62 can be mounted by means of a carriage 66 onto a worm gear 68 driven by a motor 70. The worm gear is journalled onto the base 10. The wedge member 62 is adapted to extend and move through an opening 61 in the support member 36. The wedge member acts against a push rod 64 in this same opening, moving the support member 40. As the wedge member is passed through the opening 61 by means of the motor 70 turning the worm gear 68, the cross-section of the wedge, of course, gradually increases, forcing the pressure plate 64 to push the rod 65 in the support member 40 away from the support member 36, thereby displacing the clamp bits 54 and 56 from the clamp bits 26 and 28. If a sheet of paper is being held between the bits 26 and 28, and bits 54 and 56, the movement of the wedge will force the clamps gripping the paper to tear the paper, and the amount of displacement of the wedge can be recorded at the position that the fibers in the paper were finally torn.

If it is not necessary to apply a constant rate of elongation to the paper fibers, it may be sufficient to have a pneumatic pressure means, such as those described in U.S. Pat. No. 3,707,119, which applies a constant load.

For instance, as shown in FIG. 5, within the recess 61, there can be provided a piston head 78, diaphragm 80, and piston 74 passing through a passage 76 and connected to the support member 40. As air pressure is fed into the recess 71 within the diaphragm-sealed chamber, it will force the piston head to push piston 74 to move the support member 36, thereby causing the pairs of jaws to be forced apart. A suitable control panel could be provided for operating the jaws.

A secondary or supplemental pneumatic device 82 may be necessary to provide a zero reading at the jaws. Similarly, pneumatic device 82 includes a piston head 84, diaphragm 86 in a recess 87 in the member 36, and a piston rod 88 connected to the member 40. The pneumatic device 82 may be loaded such that it equalizes the weight of the assembly of the support member 40 and jaws 42 and 44.

We claim:

1. An apparatus for testing the tensile strength of fibers in a flat sheet comprising a base, a first support member on the base, a first pair of clamping jaws mounted to said first support member and adapted to receive and clamp a sheet material to be tested, said first support member extending above said first pair of jaws, a second support member pivoted to said first support member in pendulum manner, a second pair of clamping jaws mounted on said second support member opposite to said first pair of jaws and adapted to clamp said sheet material adjacent said first pair of jaws, said second support member pivoting in a pendulum manner and being at dead center with said second pair of clamping jaws being juxtaposed and in contact with the first jaws, means for pivotally causing the movement of the second support member away from dead center such that the pairs of jaws, while still clamping said sheet material, will move apart under pressure.

2. An apparatus as defined in claim 1, wherein the pairs of jaws each include a first jaw fixed to a respective support member, a bracket suspended from and fixed to the support member, the lower jaw being provided between the bracket and the first jaw member, and fluid pressure means operating between said bracket and said lower jaw to move the lower jaw towards the fixed jaw, and compression spring means provided between the fixed jaw and the lower moving jaw to normally urge the lower jaw to an open position.

3. An apparatus as defined in claim 2, wherein the means for moving the lower jaw include large diameter, telescoping cylinders operating under low pneumatic pressure.

4. An apparatus as defined in claim 2, wherein the resilient spring means urging the lower jaw from the fixed jaw is a large, flexible, cylindrical tube made of spring material.

5. An apparatus as defined in claim 1, wherein the means for separating the second pivoting support from the fixed support include a passage provided laterally through the first support, a movable pressure member within said passage, the pressure member fixedly connected to a rod which is in turn fixed to the pivoting support member, and an elongated wedge member adapted to move at a constant rate through said passage pressing against pressure plate and forcing the pivoting support member to move away from the fixed support member, and means for advancing said wedge member at a constant rate.

6. An apparatus as defined in claim 5, wherein an additional push member is connected to the second member and extends within an opening in the first member, the opening in the first member being closed and including a pneumatic device defining a pressure chamber with a piston head connected to the push means and means for loading the pneumatic chamber against the piston head such that the pressure applied to the piston head and the second member is equal to the force required to overcome the weight of the second support member and jaw assembly.

7. An apparatus for testing the tensile strength of fibers in a flat sheet comprising a base, a first support member on the base, a first pair of clamping jaws mounted to said first support member and adapted to receive and clamp a sheet material to be tested, a second support member pivoted to the first support member, a second pair of clamping jaws mounted on said second support member opposite to said first pair of jaws and adapted to clamp said sheet material adjacent said first pair of jaws, means for pivotally causing the movement of the second support member away from the first support member while the jaws are still clamping the sheet material, including an opening provided laterally through the first support member, an elongated wedge member adapted to move at a constant rate through said passage, push rod means connected to the second support member and extending within the passage and said first member and adapted to abut against the elongated wedge member such that as the wedge member is advanced through the passage at an ever increasing width, it will move the second member away from the first member by reason of the push means being moved by the wedge member.

8. An apparatus for testing the tensile strength of fibers in a flat sheet comprising a base, a first support member on the base, a first pair of clamping jaws mounted to said first support member and adapted to receive and clamp a sheet material to be tested, a second support member pivoted to said first support member, a second pair of clamping jaws mounted on said second support member opposite to said first pair of jaws and adapted to clamp said sheet material adjacent said first pair of jaws, means for pivotally causing the movement of the second support member away from the first support member such that the pairs of jaws, while still clamping said sheet material, will move apart under pressure, each said pairs of jaws including a first jaw fixed to the respective support member and a second jaw movable to and away from the first jaw and connected to the first jaw at least by a cylindrical resilient member normally urging the second jaw away from the first jaw.

9. An apparatus as defined in claim 8, wherein the resilient cylindrical member is a flexible cylindrical tube made of spring material.

* * * * *